United States Patent [19]

Boesch

[11] 4,212,867
[45] Jul. 15, 1980

[54] 2-CYANO-5-SUBSTITUTED 1,3,4-OXADIAZOLES AND FUNGICIDAL COMPOSITIONS CONTAINING THEM

[75] Inventor: Roger Boesch, Vitry, France

[73] Assignee: Philagro, France

[21] Appl. No.: 882,061

[22] Filed: Feb. 28, 1978

[30] Foreign Application Priority Data

Mar. 3, 1977 [FR] France .................. 77 06875
Jan. 23, 1978 [FR] France .................. 78 02454

[51] Int. Cl.² ............... A01N 9/22; C07D 271/10; C07D 498/00
[52] U.S. Cl. ........................... 424/263; 546/277; 548/143; 424/272
[58] Field of Search ........ 260/307 G, 294.9, 294.8 G; 424/263, 272; 546/277

[56] References Cited

U.S. PATENT DOCUMENTS 3,718,452  2/1973  Dahle .................. 71/92

*Primary Examiner*—Anton H. Sutto
*Attorney, Agent, or Firm*—Robert E. Burns; Emmanuel J. Lobato; Bruce L. Adams

[57] ABSTRACT

1,3,4-Oxadiazole derivatives, are disclosed which correspond to the formula

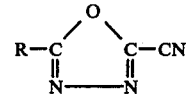

in which R represents the phenyl radical; a phenyl radical which is substituted by 1 to 5 identical or different substituents chosen from amongst halogen atoms, the nitro radical, the cyano radical, the hydroxy radical, alkyl radicals containing from 1 to 4 carbon atoms, alkoxy radicals, the alkyl part of which contains from 1 to 4 carbon atoms, alkenyl radicals containing from 2 to 4 carbon atoms, alkenyloxy radicals containing from 2 to 4 carbon atoms, alkenyl radicals containing from 2 to 4 carbon atoms, alkynyloxy radicals alkynyl part of which contains from 2 to 4 carbon atoms, alkylsulphonyl radicals, the alkyl part of which contains from 1 to 4 carbon atoms, alkylthio radicals containing 1 to 4 carbon atoms dialkylamino radicals, of which each of the identical or different alkyl parts contains from 1 to 4 carbon atoms, the carbamoyloxy radical which is optionally substituted by 1 to 2 alkyl radicals containing from 1 to 4 carbon atoms, or the trifluoromethyl radical, a phenyl radical which is substituted by a divalent alkylenedioxy radical in which the alkylene part contains from 1 to 4 carbon atoms, or a naphthyl radical or a heterocyclic radical comprising from 5 to 7 chain members and containing, as the heteroatom, a nitrogen, sulphur or oxygen atom, these radicals being optionally substituted by 1 to 3 identical or different substituents chosen from amongst halogen atoms, and alkyl, alkoxy or alkylthio radicals in which the alkyl part contains from 1 to 4 carbon atoms. These compounds can be used as agricultural fungicides.

5 Claims, No Drawings

2-CYANO-5-SUBSTITUTED 1,3,4-OXADIAZOLES AND FUNGICIDAL COMPOSITIONS CONTAINING THEM

BACKGROUND OF THE INVENTION

The present invention relates to new 1,3,4-oxadiazole derivatives and the preparation of these compounds. It also relates to the fungicidal compositions in which at least one of these new compounds is present as the active material, and to fungicidal treatments carried out using these compositions.

SUMMARY OF THE INVENTION

More precisely, the invention relates to new fungicidal compounds corresponding to the general formula:

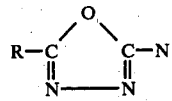

Formula A in which R represents the phenyl radical; a phenyl radical which is substituted by 1 to 5 identical or different substituents chosen from amongst halogen atoms, the nitro radical, the cyano radical, the hydroxy radical, alkyl radicals containing from 1 to 4 carbon atoms, alkoxy radicals, the alkyl part of which contains from 1 to 4 carbon atoms, alkenyl radicals containing from 2 to 4 carbon atoms, alkenyloxy radicals, the alkenyl part of which contains from 2 to 4 carbon atoms, alkynyl radicals containing from 2 to 4 carbon atoms, alkynyloxy radicals, the alkynyl part of which contains from 2 to 4 carbon atoms, alkylthio radicals, the alkyl part of which contains from 1 to 4 carbon atoms, alkylsulphonyl radicals, the alkyl part of which contains from 1 to 4 carbon atoms, alkylthio radicals containing 1–4 dialkylamino radicals, of which each of the identical or different alkyl parts contains from 1 to 4 carbon atoms, the carbamoyloxy radical which is optionally substituted by 1 to 2 alkyl radicals containing from 1 to 4 carbon atoms, or the trifluoromethyl radical; a phenyl radical which is substituted by a divalent alkylenedioxy radical in which the alkylene part contains from 1 to 4 carbon atoms; or a naphthyl radical or a heterocyclic radical comprising from 5 to 7 chain members and containing, as the heteroatom, a nitrogen, sulphur or oxygen atom, these radicals being optionally substituted by 1 to 3 identical or different substituents chosen from amongst halogen atoms, and alkyl, alkoxy or alkylthio radicals in which the alkyl part contains from 1 to 4 carbon atoms.

The invention also relates to the preparation of these compounds and to their use as fungicides.

The invention relates more particularly to the compounds of the general formula A, in which R represents a phenyl radical which is substituted by 1 to 3 identical or different substituents chosen from amongst halogen atoms, the cyano radical, alkyl radicals containing from 1 to 4 carbon atoms, alkoxy radicals containing from 1 to 4 carbon atoms, alkenyloxy radicals containing from 1 to 4 carbon atoms, alkylthio radicals containing from 1 to 4 carbon atoms, and dialkylamino radicals, of which each of the identical or different alkyl parts contains from 1 to 4 carbon atoms; or a naphthyl or pyridyl radical which is substituted by 1 to 3 identical or different substituents chosen from amongst halogen atoms, and alkyl, alkoxy or alkylthio radicals in which the alkyl part contains from 1 to 4 carbon atoms.

The invention further relates, by way of new intermediates, to the compounds corresponding to any one of the general formulae B, C and D below, in which R has the same meaning as in the formula A. In the formulae C and D, $R_1$ represents an alkyl group containing 1 to 6 carbon atoms:

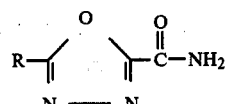

Formula B

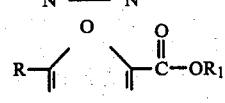

Formula C

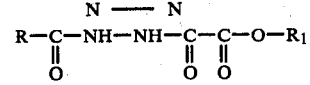

Formula D

Various 1,3,4-oxadiazole derivatives have already been described, certain of which exhibit fungicidal properties.

Thus, French Pat. No. 2,211,008 claims fungicidal compounds of the general formula:

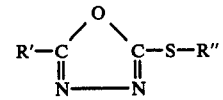

in which R' is an optionally substituted phenyl radical, a phenylalkyl or phenoxyalkyl radical, or an optionally substituted heterocyclic radical, and R" is a halogenoalkylthio, trichloromethylthio, thiocyanatoalkyl, cyano, alkenyl or alkynyl, acyl, alkoxycarbonyl, cyclohexyloxycarbonyl, alkylthiocarbonyl, amido, monoalkylamido or sulphonyl radical, the alkyl part containing from 1 to 3 carbon atoms.

The compounds claimed by the present application are different from those which form the subject of this French Pat. No. 2,211,008. The compounds of the general formula A of the present application exhibit an antifungal activity which is generally superior to, and/or different from, that of the latter compounds.

The fungicidal compounds according to the invention, which correspond to the general formula A, are obtained by dehydrating the compounds of the general formula B in accordance with the following equation:

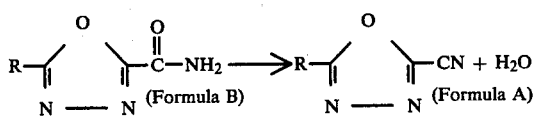

The reaction is carried out in an anhydrous inert solvent medium, at a temperature which can vary from 0° to 60° C. and in the presence of a dehydrating agent such as, for example, $POCl_3$, $P_2O_5$, $SOCl_2$ or trifluoroacetic anhydride. Organic solvents such as, for example, carbon tetrachloride, perchloroethylene, toluene and pyridine, may be mentioned as solvents which can be used. Phosphorus oxychloride can also be used as the solvent, without using any organic solvent.

The compounds of the general formula B are obtained by the ammonolysis of the compounds of the general formula C, using a process which is in itself known, in accordance with the following equation:

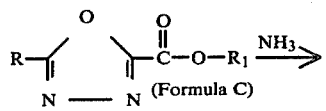

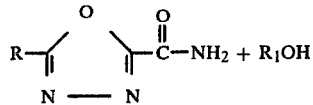

The reaction is carried out at between 0° and 30° C., using ammonia and in the presence of a lower alkanol, for example ethanol, which is by itself or mixed with an inert organic solvent, for example toluene.

The compounds of the general formula C are obtained by cyclizing the compounds of the general formula D, using a process which is in itself known, in accordance with the equation:

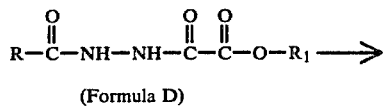

(Formula D)

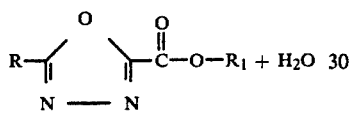

This cyclization is carried out by heating, at a temperature which can range from ambient temperature up to about 140° C., in an anhydrous inert solvent medium and in the presence of a dehydrating agent such as, for example, $P_2O_5$, $POCl_3$ or $SOCl_2$. In practice, the reaction is carried out by heating under reflux in an organic solvent which can be, for example, an aromatic hydrocarbon such as toluene, xylene or benzene, chlorobenzene or a halogen-containing aliphatic hydrocarbon such as carbon tetrachloride or perchloroethylene. Phosphorus oxychloride can also be used as the solvent, without using any organic solvent.

The compounds of the general formula D are obtained by condensing an alkyloxalyl halide with an acyl hydrazide in accordance with the equation:

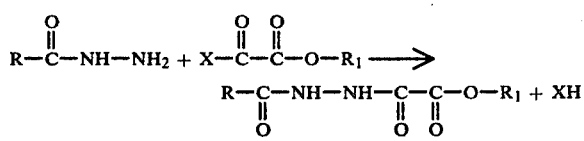

in which R and $R_1$ have the same meaning as above and X represents a halogen atom, and preferably a chlorine atom.

This reaction is carried out in an anhydrous inert organic solvent medium, in the presence of an acid acceptor such as a tertiary amine, for example pyridine or triethylamine, and at a temperature of between about 0° and 30° C.

The compounds of the general formula D can also be obtained by the action of an acid halide on an alkyl hydrazinooxalate in accordance with the equation:

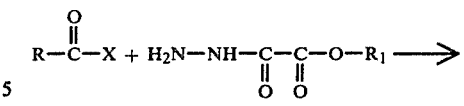

compound D + XH in which R, $R_1$ and X have the same meaning as above, the reaction being carried out in accordance with the same conditions as above.

The acyl hydrazide is itself obtained in accordance with a known process by the action of hydrazine hydrate on an ester of the general formula

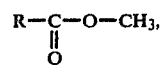

in ethanol which is heated under reflux.

The following Examples are given without implying a limitation in order to describe the preparation of the compounds according to the invention and to illustrate the fungicidal properties of the compounds corresponding to the general formula A.

EXAMPLE 1

Preparation of 2-cyano-5-(3,5-dimethylphenyl)-1,3,4-oxadiazole (compound no. 1)

200 g of phosphorus oxychloride are added to a suspension of 189.5 g of 2-carbamoyl-5-(3,5-dimethylphenyl)-1,3,4-oxadiazole in 873 cm³ of anhydrous pyridine, in the course of one hour and whilst stirring. During this addition, the temperature of the reaction medium rises from 20° to 42° C. The stirring is continued for 4 hours, whilst allowing the temperature of the medium to return to 20° C. The reaction mixture is then poured into 8.7 liters of water and the precipitate which forms is filtered off, washed twice with 500 cm³ of water and then dried in the air. After recrystallization from isopropanol, 163 g of solid 2-cyano-5-(3,5-dimethylphenyl)-1,3,4-oxadiazole, which melts at 127° C., are obtained.

Yield: 93.7%

Percentage analysis N%: Calculated 21.09; Found 21.6.

The structure of this compound was confirmed by infrared spectrography.

2-Carbamoyl-5-(3,5-dimethylphenyl)-1,3,4-oxadiazole is obtained in accordance with the following process:

A stream of ammonia is bubbled, for about 2 hours, into a solution of 260 g of 2-ethoxycarbonyl-5-(3,5-dimethylphenyl)-1,3,4-oxadiazole in 520 cm³ of ethanol and 2,600 cm³ of toluene, kept at 5° C. The stirring is continued (sic) for a further two hours, whilst allowing the temperature of the reaction medium to return to 20° C. The bulky precipitate which has appeared is filtered off, washed three times with 150 cm³ of ethanol and then dried under reduced pressure (0.5 mm of mercury) at 20° C. 211.5 g of 2-carbamoyl-5-(3,5-dimethylphenyl)-1,3,4-oxadiazole, which melts at 230° C., are thus obtained. The structure is confirmed by infrared spectrography.

2-Ethoxycarbonyl-5-(3,5-dimethylphenyl)-1,3,4-oxadiazole is obtained in accordance with the following process:

A mixture of 178.5 g of 1-ethoxalyl-2-(3,5-dimethyl-benzoyl)-hydrazine and 535 g of phosphorus pentoxide in 2.7 liters of anhydrous toluene is heated under reflux for one hour, whilst stirring vigorously. After cooling to ambient temperature, 1.6 liters of water are added to the reaction mixture, whilst cooling with a bath of ice-cooled water. The organic phase is decanted, successively washed twice with one liter of water, twice with 0.5 liter of a 10% strength aqueous solution of $CO_3HK$ and then with one liter of water, and it is finally dried over sodium sulphate. The toluene phase is combined with that obtained from a second experiment carried out under the same conditions and using the same amounts of starting materials. After the solvent has been driven off under reduced pressure (20 mm of mercury) at 40°–50° C., the residual solid is recrystallized from 1.4 liters of cyclohexane. 260 g of solid 2-ethoxycarbonyl-5-(3,5-dimethylphenyl)-1,3,4-oxadiazole, which melts at 104° C., are thus obtained. The structure is confirmed by infrared spectrography.

1-Ethoxalyl-2-(3,5-dimethylbenzoyl)-hydrazine is obtained in accordance with the following process:

265 g of ethoxalyl chloride are added, in the course of one hour, to 316 g of 3,5-dimethylbenzhydrazide and 195 g of triethylamine in 1.58 liters of anhydrous dioxane, whilst keeping the temperature of the reaction medium at about 10°–12° C. The stirring is continued (sic) for about two hours. whilst allowing the temperature to return to the ambient value. The reaction mixture is then poured into seven liters of water, whilst stirring. The precipitate which has formed is filtered off, washed three times with one liter of water and then dried at 20° C. under a pressure of one millimeter of mercury. 357 g of 1-ethoxalyl-2-(3,5-dimethylbenzoyl)-hydrazine, which melts at 159° C., are obtained.

3,5-Dimethylbenzhydrazide, which melts at 140° C., can be obtained by the action of hydrazine hydrate on methyl 3,5-dimethylbenzoate in ethanol under reflux.

EXAMPLE 2

The following compounds corresponding to the formula A were prepared from the appropriate starting materials by following the method described in Example 1.

| Compound no. | R | Melting point °C. | Percentage analysis % Calculated | | Found |
|---|---|---|---|---|---|
| 2 | phenyl | 89 | N | 24.55 | 24.15 |
| 3 | 4-F-phenyl | 73 | F | 10.04 | 9.90 |
|  |  |  | N | 22.22 | 21.95 |
| 4 | 3-F-phenyl | 113 | F | 10.04 | 10.35 |
|  |  |  | N | 22.22 | 21.85 |
| 5 | 4-Cl-phenyl | 137 | Cl | 17.24 | 17.25 |
|  |  |  | N | 20.44 | 20.3 |
| 6 | 3,4-diCl-phenyl | 117 | Cl | 29.54 | 29.80 |
|  |  |  | N | 17.51 | 17.10 |
| 7 | 3,5-diCl-phenyl | 79 | Cl | 29.54 | 28.75 |
|  |  |  | N | 17.51 | 17.25 |
| 8 | 2,3-diCl-phenyl | 111 | Cl | 29.54 | 29.40 |
|  |  |  | N | 17.51 | 17.25 |
| 9 | 2,4-diCl-phenyl | 168 | Cl | 29.54 | 28.90 |
|  |  |  | N | 17.51 | 17.35 |
| 10 | 3-Cl-4-$O_2N$-phenyl | 155 | Cl | 14.15 | 14.25 |
|  |  |  | N | 22.36 | 22.20 |
| 11 | 2,3,5-triMe-phenyl | 116 | N | 19.71 | 19.45 |
| 12 | 2,3,5-triMeO-phenyl | 138 | N | 16.08 | 15.70 |
| 13 | 2-Cl-5-MeO-6-Cl-phenyl | 144 | Cl | 26.25 | 26.25 |
|  |  |  | N | 15.36 | 15.35 |

The structure of these compounds was confirmed by infrared spectrography.

The table below indicates the melting points of compounds B2, B3 and the like, which correspond to the formula B and are used in the preparation of compounds nos. 2, 3 and the like respectively.

(Formula B)

$$R-\underset{N-N}{\overset{O\quad O}{\underset{\|}{C}-\underset{\|}{C}-NH_2}}$$

| Compound no. | R | Melting point °C. |
|---|---|---|
| B2 | phenyl | 172 |
| B3 | 4-F-phenyl | 173 |
| B4 | 3-F-phenyl | 160 |
| B5 | 4-Cl-phenyl | 230 |
| B6 | 3,4-diCl-phenyl | 223 |
| B7 | 3,5-diCl-phenyl | 182 |
| B8 | 2,3-diCl-phenyl | 235 |
| B9 | 2,4-diCl-phenyl | 206 |

-continued

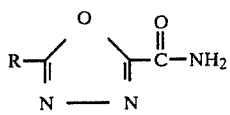 (Formula B)

| Compound no. | R | Melting point °C. |
|---|---|---|
| B10 | O$_2$N—⬡—Cl (with Cl ortho) | 204 |
| B11 | 2,4,6-trimethylphenyl (CH$_3$, CH$_3$, CH$_3$) | 185 |
| B12 | 3,4,5-trimethoxyphenyl (CH$_3$O, CH$_3$O, CH$_3$O) | 246 |
| B13 | 2,4-dichloro-5-methoxyphenyl (Cl, CH$_3$O, Cl) | 244 |

The table below indicates the melting points of compounds C2, C3 and the like, which correspond to the formula C and are used in the preparation of compounds B2, B3 and the like respectively.

$$R-\underset{N-N}{\underset{\|}{C}}\!\!\!\!\!\!\!\!\!\!\!\!\overset{O}{\diagup}\!\!\!\!\!\!\!\!\!\!\!\!\underset{}{C}-C-O-R_1$$ (Formula C)

| Compound no. | R | R$_1$ | Melting point °C. |
|---|---|---|---|
| C2 | phenyl | —C$_2$H$_5$ | 71 |
| C3 | 2-fluorophenyl | —C$_2$H$_5$ | 75 |
| C4 | 3-fluorophenyl | —CH$_3$ | 115 |
| C5 | 4-chlorophenyl | —C$_2$H$_5$ | 120 |
| C6 | 3,4-dichlorophenyl | —C$_2$H$_5$ | 86 |
| C7 | 2,5-dichlorophenyl | —C$_2$H$_5$ | 77 |
| C8 | 2,4-dichlorophenyl | —C$_2$H$_5$ | 98 |
| C9 | 3,4-dichlorophenyl | —C$_2$H$_5$ | 104 |
| C10 | 2-chloro-4-nitrophenyl (O$_2$N—⬡—Cl) | —C$_2$H$_5$ | 103 |
| C11 | 2,4,6-trimethylphenyl | —C$_2$H$_5$ | 94 |
| C12 | 3,4,5-trimethoxyphenyl | —C$_2$H$_5$ | 125 |
| C13 | 2,4-dichloro-5-methoxyphenyl | —C$_2$H$_5$ | 107 |

The table below indicates the melting points of compounds D2, D3 and the like, which correspond to the formula D and are used in the preparation of compounds C2, C3 and the like respectively.

$$R-\underset{O}{\overset{\|}{C}}-NH-NH-\underset{O}{\overset{\|}{C}}-\underset{O}{\overset{\|}{C}}-O-R_1$$ (Formula D)

| Compound no. | R | R$_1$ | Melting point in °C. |
|---|---|---|---|
| D2 | phenyl | —C$_2$H$_5$ | 138 |
| D3 | 2-fluorophenyl | —C$_2$H$_5$ | 73 |
| D4 | 3-fluorophenyl | —CH$_3$ | 143 |
| D5 | 4-chlorophenyl | —C$_2$H$_5$ | 139–148 |
| D6 | 3,4-dichlorophenyl | —C$_2$H$_5$ | 167 |

-continued $$R-\underset{\underset{O}{\|}}{C}-NH-NH-\underset{\underset{O}{\|}}{C}-\underset{\underset{O}{\|}}{C}-O-R_1 \quad \text{(Formula D)}$$

| Compound no. | R | $R_1$ | Melting point in °C |
|---|---|---|---|
| D7 | 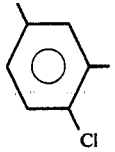 | $-C_2H_5$ | 148 |
| D8 | 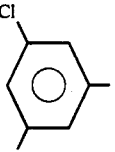 | $-C_2H_5$ | 141 |
| D9 | 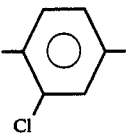 | $-C_2H_5$ | 152 |
| D10 | 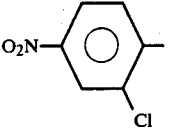 | $-C_2H_5$ | 165–169 |
| D11 | 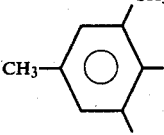 | $-C_2H_5$ | 125 |
| D12 | 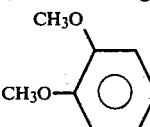 | $-C_2H_5$ | 160 |
| D13 | 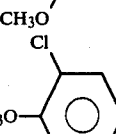 | $-C_2H_5$ | 107 |

EXAMPLE 3

Preparation of 2-cyano-5-(4-ethoxyphenyl)-1,3,4-oxadiazole (compound no. 14)

8.7 ml (14.5 g) of phosphorus oxychloride are added, in the course of 10 minutes, to a suspension of 14.7 g of 2-carbamoyl-5-(4-ethoxyphenyl)-1,3,4-oxadiazole in 126 ml of anhydrous pyridine, whilst stirring.

During this addition, the temperature of the reaction medium rises from 20° to 25° C. The stirring is continued for 2 hours, whilst allowing the temperature of the medium to return to 20° C. The reaction mixture is then poured into 1,260 ml of water and the precipiate which forms is filtered off, washed twice with 50 ml of water and then dried at 50° C. under a pressure of 1 mm Hg. 13 g of a crude product, which melts at 110° C., are obtained. This crude product is taken up in 260 ml of methylene chloride and the coloured solution obtained is stirred for 10 minutes in the presence of kieselguhr. The kieselguhr is filtered off and then washed with methylene chloride. After this treatment, the solution is colourless. It is concentrated at 60° C. under a pressure of 20 mm Hg and the solid residue is recrystallized from isopropanol. 12.3 g of 2-cyano-5-(4-ethoxyphenyl)-1,3,4-oxadiazole, which melts at 110° C., are thus obtained.

| Percentage analysis | | |
|---|---|---|
| | Calculated | Found |
| N% | 19.45 | 19.35 |

Preparation of 2-carbamoyl-5-(4-ethoxyphenyl)-1,3,4-oxadiazole used as the starting material in the preparation of compound no. 14.

A stream of ammonia is bubbled for one hour into a solution of 17.1 g of 2-ethoxycarbonyl-5-(4-ethoxyphenyl)-1,3,4-oxadiazole in 171 ml of toluene and 34 ml of ethanol, kept at between 5° and 10° C. The stirring is continued (sic) for a further two hours, whilst allowing the temperature of the reaction medium to return to 20° C. The bulky precipitate which has appeared is filtered off, washed three times with 20 ml of ethanol and then dried at 20° C. under a pressure of 1 mm Hg. 14.8 g of 2-carbamoyl-5-(4-ethoxyphenyl)-1,3,4-oxadiazole, which melts at 188° C., are thus obtained with a yield of 97.4%. The structure is confirmed by infrared spectrography.

Preparation of 2-ethoxycarbonyl-5-(4-ethoxyphenyl)-1,3,4-oxadiazole

A solution of 22 g of 1-ethoxalyl-2-(4-ethoxybenzoyl)-hydrazine and 28 g of thionyl chloride in 157 ml of anhydrous 1,2-dichloroethane is heated under reflux, whilst stirring vigorously, until the evolution of gas has ceased (that is to say about 4 hours). The solvent and excess thionyl chloride are driven off in vacuo (50° C., 20 mm Hg). The residue is taken up in 150 ml of methylene chloride and the methylene chloride solution is successively washed with 2×30 ml of water, then with 30 ml of a 20% strength potassium bicarbonate solution and then with 2×30 ml of water. It is dried over anhydrous sodium sulphate. The solvent is driven off under reduced pressure (20 mm Hg, 50° C.). The solid residue is then recrystallized from isopropanol. 15.9 g of 2-ethoxycarbonyl-5-(4-ethoxyphenyl)-1,3,4-oxadiazole, which melts at 93° C., are obtained. The structure is confirmed by infrared spectrography.

Preparation of 1-ethoxalyl-2-(4-ethoxybenzoyl)-hydrazine 29 g of ethoxalyl chloride are added, in the course of 30 minutes, to 36 g of 4-ethoxybenzhydrazide and 21.3 g of triethylamine in 360 ml of anhydrous dioxane, whilst keeping the temperature of the reaction medium at about 10° C. The stirring is continued (sic) for about two hours, whilst allowing the temperature to return to the ambient value. The reaction mixture is filtered, the filtrate is concentrated under reduced pressure (20 mm Hg, 50° C.) and the residue is stirred in the presence of 200 ml of isopropyl ether and then filtered off. After drying (20° C., 1 mm Hg), 50.8 g of 1-ethoxalyl-2-(4- ethoxybenzoyl)-hydrazine, which melts at 126° C. after a first melting at 120° C., are obtained. Yield: 90.7%.

4-Ethoxybenzhydrazide, which melts at 125° C., can be obtained by the action of hydrazine hydrate on methyl 4-ethoxybenzoate in ethanol under reflux.

EXAMPLE 4

The following compounds were prepared from the appropriate starting materials by following the method described in the preceding example.

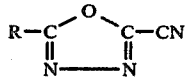

| Compound no. | R | Melting point °C. | % Calculated | % Found |
|---|---|---|---|---|
| 15 | CH₃O—⟨○⟩— , Cl | 124 | Cl 15.05<br>N 17.83 | 14.95<br>17.55 |
| 16 | CH₃O—⟨○⟩— , CH₃ | 85 | N 21.09 | 20.30 |
| 17 | CH₃, ⟨○⟩, CH₃ | 72 | N 21.09 | 20.5 |
| 18 | CH₃O—⟨○⟩— | 124 | N 20.89 | 20.65 |
| 19 | NC—⟨○⟩— | 161 | N 28.56 | 28.5 |
| 20 | CH₃—⟨○⟩— | 100 | N 22.69 | 21.90 |
| 21 | F—⟨○⟩— | 76 | F 10.04<br>N 22.22 | 9.75<br>21.80 |
| 22 | CH₃O, ⟨○⟩—, CH₃O | 113 | N 18.18 | 17.9 |
| 23 | CH₃—⟨○⟩—, CH₃ | 89 | N 21.09 | 20.5 |
| 24 | I—⟨○⟩— | 173 | I 42.72<br>N 14.14 | 42.65<br>14.15 |
| 25 | F, ⟨○⟩, Br | 98 | Br 29.81<br>F 7.09<br>N 15.58 | 29.55<br>7.1<br>15.65 |
| 26 | H₂C(O)(O)—⟨○⟩— | 157 | N 19.53 | 19.50 |
| 27 | Cl—⟨N⟩—Cl (pyridyl) | 78 | Cl 29.42<br>N 23.24 | 29.45<br>23.4 |
| 28 | ⟨○⟩—, I | 95 | I 42.72<br>N 14.14 | 42.45<br>14.0 |
| 29 | (CH₃)₂N—⟨○⟩— | 203 | N 26.15 | 26.35 |
| 30 | naphthyl | 101 | N 19.00 | 19.2 |
| 31 | Br—⟨○⟩— | 158 | Br 31.96<br>N 16.80 | 32.95<br>17.40 |
| 32 | OCH₃, ⟨N⟩, OCH₃ (pyridyl) | 120 | N 24.13 | 24.27 |
| 33 | CH₃S—⟨○⟩— | 135 | N 19.34<br>S 14.76 | 19.33<br>14.43 |
| 34 | (CH₃)₂CHO—⟨○⟩— | 98 | N 18.33 | 18.55 |
| 35 | CH₃(CH₂)₂O—⟨○⟩— | 81 | N 18.33 | 18.35 |
| 36 | CH₂=CH—CH₂O—⟨○⟩— | 84 | N 18.49 | 18.3 |
| 37 | Cl—⟨○⟩—, CH₃ | 150 | Cl 16.14<br>N 19.13 | 16.15<br>19.3 |
| 38 | Br—⟨○⟩—, CH₃ | 174 | Br 30.26<br>N 15.91 | 30.1<br>16.1 |
| 39 | ⟨○⟩—, Cl | 75 | Cl 17.24<br>N 20.44 | 17.25<br>20.6 |
| 40 | ⟨○⟩—, Br | 70 | Br 31.95<br>N 16.80 | 32.4<br>16.75 |
| 41 | ⟨○⟩—, CH₃O | 100 | N 20.89 | 20.80 |
| 42 | ⟨○⟩—, Br | 69 | Br 31.95<br>N 16.80 | 32.35<br>16.80 |
| 43 | CH₃—⟨○⟩—, Cl | 115 | Cl 16.14<br>N 19.13 | 16.10<br>18.90 |

| Compound no. | R | Melting point °C. | Percentage analysis % Calculated | % Found |
|---|---|---|---|---|
| 44 | (2-C₂H₅O-phenyl) | 132 | N 19.52 | 19.30 |
| 45 | (3-OCH₃-phenyl) | 69 | N 20.89 | 20.75 |

Structure:
R—C(=N—N=)—O—C—CN (oxadiazole with R and CN substituents)

EXAMPLE 5

In vitro test of fungicidal activity

For this experiment, a series of test tubes is used, each of which contains 4 ml of an artificial culture medium (Sabouraud's agar).

After these have been sterilized in an autoclave, 2 ml of a suspension in water of the active material to be tested is added to each tube, using different concentrations of active material. This suspension also contains 0.02% by weight of a condensate of sorbitol monooleate with 10 mols of ethylene oxide.

A suspension of spores in sterile distilled water, which contains about $4.10^{-6}$ spores/ml, is prepared for various species of fungi and each tube is inoculated with 0.25 ml of this suspension. After inoculation, the tubes are kept in an oven at 25° C. for nine days.

On the ninth day of culture, the percentage inhibition of the growth of each species of fungus is evaluated for various concentrations of active material. The minimum concentration of the product which causes 95 to 100% inhibition of the growth of the fungi, which is called "minimum inhibitory concentration", is determined from these results for each species of fungus. This concentration is expressed in mg of active material per liter of suspension; the results relating to the compounds tested are reported in the table below:

Saccharomyces pastorianus = Sa.pa
Fusarium oxysporum = Fu.ox
Botrytis cinerea = Bo.ci
Trichophyton mentagrophyte = Tr.me
Candida albicans = Ca.al
Penicillium digitatum = Pe.di
Rhizopus nigricans = Rh.ni
Aspergillus niger = As.ni

| Compound no. | Sa.pa | Fu.ox | Bo.ci | Tr.me | Ca.al | Pe.di | Rh.ni | As.ni |
|---|---|---|---|---|---|---|---|---|
| 1 | 4 | 18 | 18 | 1 | 15 | 8 | >500 | 25 |
| 2 | 31 | 50 | 50 | 10 | 50 | 30 | 30 | 40 |
| 3 | 15 | 62 | 15 | 8 | 62 | 62 | 10 | 125 |
| 4 | 10 | 35 | 30 | 20 | 50 | 40 | 50 | 75 |
| 5 | 7 | 7 | 10 | 5 | 10 | 5 | 15 | 20 |
| 6 | 2 | 5 | 10 | 1.5 | 5 | 5 | 400 | 15 |
| 7 | 12 | 7 | 10 | 60 | 10 | 8 | 70 | 18 |
| 8 | 2 | 15 | 12 | 2 | 7 | 10 | >500 | 20 |
| 9 | 7 | 25 | 10 | 5 | 7 | 10 | >500 | 40 |
| 10 | 20 | 35 | 40 | 7 | 40 | 50 | 100 | 60 |
| 11 | 3 | 8 | 15 | 2.5 | 4 | 5 | >500 | 18 |
| 12 | 50 | 100 | >500 | 20 | >500 | 70 | >500 | >500 |
| 14 | 4 | 50 | 5 | 1 | 10 | 4 | >500 | 8 |
| 15 | 5 | 10 | 10 | 5 | 15 | 7 | >500 | 20 |
| 16 | 5 | 8 | 8 | 4 | 7 | 1 | >500 | 10 |
| 17 | 3 | 6 | 6 | 3 | 8 | 5 | 250 | 8 |
| 18 | 5 | 7 | 7 | 2 | 8 | 5 | 30 | 8 |
| 19 | 12 | 15 | 10 | 4 | 16 | 8 | 30 | 30 |
| 20 | 4 | 5 | 5 | 1 | 8 | 2 | 20 | 8 |
| 21 | 10 | 6 | 3 | 1 | 5 | 4 | 12 | 3 |
| 22 | 60 | 15 | 30 | 3 | 20 | 16 | >500 | 100 |
| 23 | 2 | 5 | 5 | 1 | 5 | 4 | 150 | 5 |
| 24 | 16 | 8 | 16 | 3 | 16 | 12 | >500 | 16 |
| 25 | 8 | 8 | 8 | 4 | 16 | 8 | 70 | 30 |
| 26 | 3 | 10 | 10 | 1 | 7 | 4 | 40 | 8 |
| 27 | 4 | 15 | 10 | 4 | 10 | 10 | 70 | 50 |
| 28 | 4 | 7 | 6 | 2 | 7 | 5 | 40 | 7 |
| 29 | 8 | 50 | 50 | 2 | >500 | 7 | >500 | 500 |
| 30 | 3 | 3 | 40 | 1 | 5 | 4 | 12 | 10 |
| 31 | 5 | 6 | 6 | 1 | 4 | 2 | 250 | 10 |
| 32 | 8 | 15 | 15 | 4 | 20 | 10 | >500 | 40 |
| 33 | 2 | 500 | 4 | 0.5 | 4 | 1 | >500 | 4 |
| 34 | 4 | 65 | 8 | 1 | 10 | 2 | >500 | 8 |
| 35 | 2 | 40 | 8 | 1 | 6 | 1.5 | >500 | 5 |
| 36 | 3 | 70 | 7 | 1 | 4 | 2 | >500 | 5 |
| 37 | 2 | 8 | 5 | 1 | 2 | 2 | >500 | 7 |
| 38 | 6 | 125 | >500 | 4 | 6 | 6 | >500 | 500 |
| 39 | 4 | 30 | 4 | 2 | 4 | 4 | 20 | 8 |
| 40 | 4 | 75 | 10 | 2 | 10 | 4 | 75 | 15 |
| 41 | 10 | 60 | 10 | 4 | 20 | 5 | 60 | 20 |
| 42 | 4 | 75 | 10 | 0.5 | 10 | 5 | 40 | 20 |

EXAMPLE 6

Greenhouse test on anthracnosis in beans

Bean seedlings (*Phaseolus vulgaris*) of the Michelet variety are cultivated in pots. When these seedlings are about 12 days old (stage at which the cotyledonary leaves are totally developed), they are treated by spraying each of them with 4 ml of an aqueous suspension of active material, which is at the desired concentration and contains 0.02% of a condensate of sorbitol monooleate with 10 mols of ethylene oxide. Spraying is repeated eight times for each concentration. The reference seedlings are treated under the same conditions but without active material. After drying for 4 hours, each seedling is contaminated with 1 ml of a suspension of spores ($10^6$ spores) of *Colletotrichum lindemuthianum*, which is responsible for anthracnosis in beans, and the seedlings are then incubated for 7 days at about 22° C. and 80% relative humidity.

The minimum concentration causing 95-100% inhibition of the parasite is determined 7 days after contamination.

Under these conditions, this concentration is found to be respectively:
- 31 mg/l for compound no. 18
- 100 mg/l for compound no. 26
- 125 mg/l for compound no. 22
- 200 mg/l for compound no. 37
- 250 mg/l for compounds nos. 6, 9, 12, 13, 20, 23, 32, 34, 35, 38, 43 and 44
- 300 mg/l for compound no. 30
- 400 mg/l for compounds nos. 1 and 25
- 500 mg/l for compounds nos. 4, 10, 14, 15, 17, 24, 28, 36 and 40.

EXAMPLE 7

Greenhouse test on tomato mildew

The procedure of Example 6 is followed, except that the plants are tomato seedlings (*Lycopersicum esculentum*) of the Marmande variety. They are treated when they are about 1 month old (5- to 6-leaf stage, height 12 to 15 cm) and then contaminated with spores of Phytophthora infestans, which is responsible for tomato mildew, at a rate of about $2.10^5$ spores per plant. Under these conditions, the minimum concentrations (in mg/l) which cause 95-100% inhibition of the parasite in question, are found to be respectively as follows:
- 62 (compounds 8 and 18)
- 100 (compound 31)
- 125 (compounds 1, 5, 14, 23, 25, 27, 28, 32, 35, 40, 41 and 42)
- 150 (compound 26)
- 200 (compound 6)
- 250 (compounds 15, 16, 19, 22, 29, 33, 34 and 39)
- 350 (compounds 17 and 37)
- 500 (compounds 7, 20 and 20)
- 750 (compounds 2, 21 and 24)

EXAMPLE 8

Greenhouse test on tobacco mildew

The procedure of Example 6 is followed, except that the plants are tobacco seedlings (*Nicotina tabacum*) of the Samson variety. They are treated when they are about one month old (5- to 6-leaf stage, height 10 to 12 cm) and then contaminated with spores of *Peronospora tabacina*, which is responsible for tobacco mildew, at a rate of about $2.10^5$ spores per plant.

Under these conditions, the minimum concentrations, expressed in mg/l, which cause from 95 to 100% inhibition of the parasite in question, are found to be respectively as follows:
- 62 (compounds nos. 8, 18, 23 and 37)
- 75 (compounds nos. 1, 9, 17 and 32)
- 100 (compounds nos. 11, 28 and 35)
- 125 (compounds nos. 4, 6, 7, 14, 27, 34, 39, 40, 41 and 42)
- 150 (compound no. 22)
- 250 (compounds nos. 3, 5, 13, 20, 21, 30 and 31)
- 300 (compound no. 16)
- 500 (compounds nos. 15, 25 and 38)

EXAMPLE 9

Greenhouse test on cucumber oidium

The procedure of Example 6 is followed, except that the plants are cucumber seedlings (*Cucumis sativus*) of the Blanc hatif variety and that the treatment with the aqueous suspension of active material is carried out after contamination (curative treatment). To do this, the 3 to 4 week old cucumber seedlings (1- or 2-leaf stage, height 6 to 10 cm) are contaminated with spores of Erysiphe cichoracearum, which is responsible for cucumber oidium, at a rate of about $7.5.10^5$ spores per plant. Eight days after contamination, the seedlings are treated with the aqueous suspension of active material in accordance with the conditions indicated in Example 4. The results are evaluated seven days after the curative fungicidal treatment.

Under these conditions, the minimum concentrations (expressed in mg/l) which cause from 95 to 100% inibition of the parasite in question, are found to be respectively:
- 250 (compounds 33 and 35)
- 300 (compound 8)
- 400 (compound 7)
- 500 (compounds 23, 27, 34 and 36)
- 750 (compounds 2, 24, 25, 31, 37, 41 and 42)
- 1,000 (compounds 11, 14, 17, 18, 29, 30, 38, 39 and 40)

EXAMPLE 10

Greenhouse test on wheat rust

The procedure of Example 6 is followed, except that the plants are wheat plantlets (*Triticum sativum*) of the Etoile de Choisy variety and that observation is carried out 14 days after contamination. They are treated when they are seven days old (one-leaf stage, height 9 to 10 cm) and then contaminated with spores of Puccinia glumarum, which is responsible for wheat rust, at a rate of about $7.5.10^5$ spores per pot.

Under these conditions, the minimum concentrations (in mg/l) which cause from 95 to 100% inhibition of the parasite in question, are found to be respectively as follows:
- 62 (compounds 9, 18 and 20)
- 100 (compounds 1, 23 and 31)
- 125 (compounds 5, 6, 14, 15, 16, 17, 19, 22, 25, 32, 33, 36, 37 and 40)
- 150 (compounds nos. 24 and 30)
- 200 (compound 42)
- 250 (compounds 21, 26, 27, 29, 34, 35, 38 and 39)

These examples demonstrate clearly the excellent fungicidal activity of the compounds according to the invention on fungi belonging to various families such as, in particular: phycomycetes (*Perosnopora tabacina* and *Phythothora infestans*), ascomycetes (*Erisiphe cichoracearum*), basidiomycetes (*Puccinia glumarum*), Fungi imperfecti (*Fusarium oxysporum, Botrytis cinerea, Penicillium digitatum* and *Colletotrichum lindemuthianum*).

Particularly valuable results were obtained in the case of the following compounds: 2-cyano-5-(4-ethoxyphenyl)-1,3,4-oxadiazole, 2-cyano-5-(2,4-dichlorophenyl)-1,3,4-oxadiazole, 2-cyano-5-(3,5-dichlorophenyl)-1,3,4-oxadiazole, 2-cyano-5-(3,5-dimethylphenyl)-1,3,4-oxadiazole, 2-cyano-5-(3,5-dimethoxyphenyl)-1,3,4-oxadiazole, 2-cyano-5-(4-methylthiophenyl)-1,3,4-oxadiazole, 2-cyano-5-(3-methyl-4-chlorophenyl)-1,3,4-oxadiazole, 2-cyano-5-(3-methyl-4-bromophenyl)-1,3,4-oxadiazole and 2-cyano-5-(2,6-dimethoxypyrid-3-yl)-1,3,4-oxadiazole.

The compounds according to the invention can therefore be used for combating fungal diseases in plants and, in particular, in wheat, tobacco, market crops, vines and fruit trees. The use doses vary within wide limits depending on the plant treated, the stage at which it is treated, the soil and the climatic conditions. In general, doses of between 0.001 and 5 g/liter are very suitable.

For use in practice, the compounds according to the invention are not generally employed by themselves. Most frequently, they form part of compositions which generally comprise, in addition to the active material according to the invention, a carrier and/or a surface-active agent which are acceptable for the plants. The proportion of active material in these compositions can vary within wide limits. In practice, this proportion of active material is preferably between 5 and 95% by weight.

The term "carrier", for the purpose of the present description, denotes an organic or inorganic, natural or synthetic material with which the active material is combined in order to facilitate its application to the plant, to the seed or to the ground, or in order to facilitate its transport or handling. The carrier can be solid (clays, natural or synthetic silicates, resins, waxes, solid fertilizers or the like) or fluid (water, alcohols, ketones, petroleum fractions, chlorohydrocarbons or liquefied gases).

The surface-active agent can be an emulsifier, dispersing agent or wetting agent and can be ionic or non-ionic. Examples which may be mentioned are salts of polyacrylic acids and of ligninsulphonic acids, and condensates of ethylene oxide with fatty alcohols, fatty acids or fatty amines.

The compositions according to the invention can be prepared in the form of wettable powders, dusting powders, solutions, emulsifiable concentrates, emulsions, suspension concentrates and aerosols.

The wettable powders according to the invention can be prepared, for example by grinding the active material with the solid carrier, so that they contain from 20 to 95% by weight of a dispersing agent and, where necessary, from 0 to 10% by weight of one or more stabilizers and/or other additives such as penetrating agents, adhesives or anti-caking agents, dyestuffs and the like.

By way of example, the composition of a wettable powder is given, the percentages being expressed by weight:

| | |
|---|---|
| active material (compound no. 8) | 50% |
| calcium lignosulphonate (deflocculant) | 5% |
| isopropylnaphthalene sulphonate (wetting agent) | 1% |
| anti-caking silica | 5% |
| filler (kaolin) | 39% |

Powders for treating seeds or dusting powders are usually prepared in the form of a dust concentrate having a concentration which is similar to that of a wettable powder but without the dispersing agent; they can be diluted on site by means of a complementary amount of fluid carrier so that a composition is obtained which can conveniently coat the grains to be treated and which usually contains from 0.5 to 10% by weight of active material.

By way of example, the composition of a powder for treating seeds is given:

| | |
|---|---|
| active material, compound no. 19 | 50% |
| anionic wetting agent | 1% |
| anti-caking silica | 6% |
| kaolin (filler) | 43% |

The emulsifiable concentrates which can be applied by spraying, after dilution with water, usually contain the active material in solution in a solvent and, in addition to the solvent and where necessary, in a co-solvent, and from 10 to 50% by weight/volume of suitable additives such as stabilizers, penetrating agents, corrosion inhibitors, and dyestuffs and adhesives.

By way of example, the composition of an emulsifiable concentrate is given, the amounts being expressed in g/liter:

| | |
|---|---|
| active material | 400 g/l |
| dodecylbenzenesulphonate | 24 g/l |
| nonylphenol containing 10 molecules of ethylene oxide | 16 g/l |
| cyclohexanone | 200 g/l |
| aromatic solvent, q.s.p. | 1 liter |

The suspension concentrates, which can also be applied by spraying, are prepared so that a stable fluid product is obtained which does not form a deposit, and they usually contain from 10 to 75% by weight of active material, from 0.5 to 15% by weight of surface-active agents, from 0.1 to 10% by weight of anti-sedimentation agents such as protective colloids and thixotropic agents, from 0 to 10% by weight of suitable additives such as anti-foam agents, corrosion inhibitors, stabilizers, penetrating agents and adhesives, and, as the carrier, water or an organic liquid in which the active material is essentially insoluble; certain solid organic materials or inorganic salts can be dissolved in the carrier to assist the prevention of sedimentation or in the water as anti-freezes.

Aqueous dispersions and aqueous emulsions, for example compositions obtained by diluting a wettable powder or an emulsifiable concentrate, according to the invention, with water, at a rate of 0.1 to 500 g of active material per hectoliter of water, are included in the general scope of the present invention. These emulsions can be of the water-in-oil type or of the oil-in-water type and they can have a thick consistency such as that of a "mayonnaise".

The compositions according to the invention can contain other ingredients, for example protective colloids, adhesives or thickeners, thixotropic agents, stabilisers or sequestering agents, as well as other known active materials having pesticidal properties, in particular insecticidal or fungicidal properties.

I claim:

1. A compound of the formula

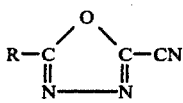

in which R represents:
the phenyl radical;
a phenyl radical which is substituted by 1 to 3 identical or different substituents chosen from amongst halogen atoms, the nitro radical, the cyano radical, alkyl radicals containing from 1 to 4 carbon atoms, alkoxy radicals, the alkyl part of which contains from 1 to 4 carbon atoms, alkylsulphonyl radicals, the alkyl part of which contains from 1 to 4 carbon atoms, alkylthio radicals containing 1 to 4 carbon atoms, dialkylamino radicals, of which each of the identical or different alkyl parts contains from 1 to 4 carbon atoms, the carbamoyloxy radical which is optionally substituted by 1 to 2 alkyl radicals containing from 1 to 4 carbon atoms, or the trifluoromethyl radical;
a phenyl radical which is substituted by a divalent alkylenedioxy radical in which the alkylene part contains from 1 to 4 carbon atoms;
a naphthyl radical or;
a pyridyl radical optionally substituted by 1 to 2 identical or different substituents chosen from amongst halogen atoms, and alkoxy radicals containing from 1 to 4 carbon atoms.

2. Process for combating fungal diseases in plants, which comprises applying a fungicidally effective amount of a compound defined in claim 1 to said plants.

3. A compound according to claim 1, in which the radical R represents a phenyl radical which is substituted by 1 to 3 identical or different substituents chosen from amongst halogen atoms, the cyano radical, alkyl radicals containing from 1 to 4 carbon atoms, alkoxy radicals containing from 1 to 4 carbon atoms, alkylthio radicals containing from 1 to 4 carbon atoms, and dialkylamino radicals, of which each of the identical or different alkyl parts contains from 1 to 4 carbon atoms;
a naphthyl radical or
a pyridyl radical which is substituted by 2 chlorine atoms or 2 methoxy atoms.

4. A fungicidal composition for the treatment of plants, containing as the active material, an effective amount of at least one compound according to claim 1 in combination with at least one agriculturally acceptable carrier and at least one agriculturally acceptable surface active agent.

5. Composition according to claim 4, in which the proportion of active material is between 5 and 95% by weight.

* * * * *